(12) United States Patent
Cayer et al.

(10) Patent No.: US 9,340,704 B2
(45) Date of Patent: May 17, 2016

(54) SUNLIGHT CURABLE COATING COMPOSITIONS

(71) Applicant: Dymax Corporation, Torrington, CT (US)

(72) Inventors: Christopher Alan Cayer, Bristol, CT (US); James Aerykssen, Torrington, CT (US); Ahmet Nebioglu, Winsted, CT (US)

(73) Assignee: Dymax Corporation, Torrington, CT (US)

( * ) Notice: Subject to any disclaimer, the term of this patent is extended or adjusted under 35 U.S.C. 154(b) by 10 days.

(21) Appl. No.: 14/248,280

(22) Filed: Apr. 8, 2014

(65) Prior Publication Data

US 2015/0284589 A1    Oct. 8, 2015

(51) Int. Cl.
| | |
|---|---|
| *C08G 18/10* | (2006.01) |
| *C09D 175/16* | (2006.01) |
| *B05D 3/06* | (2006.01) |
| *C08G 18/67* | (2006.01) |
| *C08G 18/32* | (2006.01) |

(52) U.S. Cl.
CPC .............. *C09D 175/16* (2013.01); *B05D 3/067* (2013.01); *C08G 18/3228* (2013.01); *C08G 18/672* (2013.01); *C08G 18/673* (2013.01)

(58) Field of Classification Search
CPC ... C08G 18/672; C08G 18/673; C09D 175/16
See application file for complete search history.

(56) References Cited

U.S. PATENT DOCUMENTS

| | | | | |
|---|---|---|---|---|
| 4,097,439 | A | * | 6/1978 | Darling .......................... 525/445 |
| 5,328,805 | A | * | 7/1994 | Huynh-Tran ........... C08G 18/12 |
| | | | | 430/270.1 |
| 5,684,081 | A | | 11/1997 | Dannhorn et al. |
| 2007/0021553 | A1 | * | 1/2007 | Lichte et al. .................. 524/591 |
| 2008/0306221 | A1 | | 12/2008 | Kania |
| 2009/0098305 | A1 | | 4/2009 | Cheng et al. |
| 2012/0041131 | A1 | | 2/2012 | Sommer et al. |
| 2012/0070659 | A1 | * | 3/2012 | Nakagawa ......... C08G 18/3234 |
| | | | | 428/355 AC |

FOREIGN PATENT DOCUMENTS

| | | |
|---|---|---|
| EP | 0753531 A1 | 1/1997 |
| EP | 2316867 A1 | 4/2011 |
| EP | 2431437 A1 | 3/2012 |
| WO | 2012130603 A1 | 10/2012 |

OTHER PUBLICATIONS

European Patent Office Search Report and Written Opinion for corresponding application EP15162744.

* cited by examiner

*Primary Examiner* — Michael L Leonard
(74) *Attorney, Agent, or Firm* — Roberts & Roberts, LLP

(57) ABSTRACT

A coating composition capable of curing to a high hardness by exposure to sunlight. More particularly, the coating composition comprises a high molecular weight polyurethane (meth)acrylate or methacrylate dissolved in one or more non-alcohol solvent, a visible light photoinitiator, and an alcohol solubilizer.

20 Claims, No Drawings

SUNLIGHT CURABLE COATING COMPOSITIONS

BACKGROUND OF THE INVENTION

1. Field of the Invention

The present invention relates to a coating composition capable of curing to a high hardness by exposure to sunlight. More particularly, the coating composition comprises a high molecular weight polyurethane acrylate or methacrylate dissolved in one or more non-alcohol solvents, a visible light photoinitiator, and an alcohol solubilizer. Coatings derived from this composition have many desirable properties after evaporation of the solvents, namely a tack free surface, good hardness, good flexibility, and abrasion resistance. It has been found that the physical properties of the coating, particularly pencil hardness, are further enhanced with exposure to ambient sunlight. These sunlight cured coatings have superior hardness properties to coatings cured with traditional UV light curing equipment. The superiority of the sunlight cured coatings is mainly due to the coating forming a hard film after the solvent has evaporated. This film forms a barrier between the atmosphere and an acrylate or methacrylate in the system thus reducing the effect of oxygen inhibition. Without oxygen inhibition, the film can continue to crosslink and polymerize under low intensity light thereby improving the physical properties.

2. Description of the Related Art

There is great commercial interest in coatings which have good film forming capability, dry to be essentially tack-free when solvents are evaporated, and have a resulting high degree of pencil hardness after curing over time in sunlight. These coating compositions are different from other traditional coatings in several ways. These include simplicity, absence of a need to contain film formers such as nitrocellulose, cellulose acetate butyrate, or cellulose acetate propionate which are typically used in the art to produce solid films without light curing. Other materials, additives, or plasticizers that might be typically found in the art to improve flexibility are not required, although they may optionally be included. Also single coatings derived from the compositions have good hardness without being too brittle.

SUMMARY OF THE INVENTION

The invention provides a liquid, curable coating composition comprising in admixture:

(a) one or more polyurethane film-forming polymers having the formula

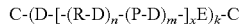

wherein:
  i) D is a residue of a diisocyanate group,
  ii) R is a residue of one or more diol or triol groups having a molecular weight less than or equal to 500 Daltons;
  iii) P is a residue of one or more oligomeric diol groups having a molecular weight of from about 500 Daltons to about 3000 Daltons;
  iv) E is a residue of a urea group having a molecular weight less than or equal to 500 Daltons;
  v) C is a residue of a monohydroxyl functional acrylate group or methacrylate group;
  wherein the equivalent ratio of (i) to (ii) is less than 1.5:1; and the equivalent ratio of (i) to (iii) is greater than 15:1; n=20 to 450, m=01 to 5,
  x=1 to 10, and k=1 to 10;
(b) an alcohol solubilizer;
(c) a non-alcohol solvent;
(d) a photoinitiator in an amount sufficient to polymerize the polyurethane film-forming polymers when exposed to light energy having a wavelength of 395 nm or above at an energy level of about 1 J/cm² or more.

The invention also provides a method of forming a substantially tack-free coating which comprises:

I) forming a liquid, curable coating composition comprising in admixture:
(a) one or more polyurethane film-forming polymers having the formula $$C\text{-}(D\text{-}[\text{-}(R\text{-}D)_n\text{-}(P\text{-}D)_m\text{-}]_x E)_k\text{-}C$$

wherein:
  i) D is a residue of a diisocyanate group,
  ii) R is a residue of one or more diol or triol groups having a molecular weight less than or equal to 500 Daltons;
  iii) P is a residue of one or more oligomeric diol groups having a molecular weight of from about 500 Daltons to about 3000 Daltons;
  iv) E is a residue of a urea group having a molecular weight less than or equal to 500 Daltons;
  v) C is a residue of a monohydroxyl functional acrylate group or methacrylate group;
  wherein the equivalent ratio of (i) to (ii) is less than 1.5:1; and the equivalent ratio of (i) to (iii) is greater than 15:1; n=20 to 450, m=01 to 5,
  x=1 to 10, and k=1 to 10;
(b) an alcohol solubilizer;
(c) a non-alcohol solvent;
(d) a photoinitiator in an amount sufficient to polymerize the polyurethane film-forming polymers when exposed to light energy having a wavelength of 395 nm or above at an energy level of about 1 J/cm² or more;

II) applying the coating composition onto a substrate following by evaporating the non-alcohol solvent and alcohol solubilizer to form substantially tack-free coating;

III) exposing the composition resulting from step II) to light energy having a wavelength of 395 nm or above at an energy level of about 1 J/cm² or more.

DESCRIPTION OF THE INVENTION

The polyurethane film-forming polymers which form a part of the invention are polyurethane acrylates and polyurethane methacrylates, which are herein generically represented by the term polyurethane (meth)acrylates. These high molecular weight polyurethane (meth)acrylates have an average molecular weight of from about 10,000 to about 100,000 Daltons, and have a composition different from tradition polyurethane (meth)acrylates in order to meet the desired physical property criteria.

Generally, traditional polyurethane (meth)acrylates have a structure according to Formula 1. However, the polyurethane (meth)acrylates according to this invention have Formula 2:

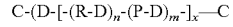   Formula 1 (Traditional)

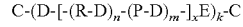   Formula 2 (Invention)

wherein D is a diisocyanate, P is one or more oligomeric diols having a molecular weight of from about 500 Daltons to about 3000 Daltons, R is one or more diols or triols having a molecular weight less than or equal to 500 Daltons. Also, the polyurethane (meth)acrylates used in the discovered composition are chain extended with a urea group as in Formula (2) wherein E is a urea group having a molecular weight less than or equal to 500 Daltons, and C is a monoalcohol (meth)

acrylate capping agent. The difference between the polyurethane (meth)acrylate used in the inventive composition (Formula 2) and traditional polyurethane (meth)acrylates (Formula 1) is that its structure is primarily derived from the (R-D) repeating units rather than the (P-D) repeating units. Specifically, the polyurethane (meth)acrylate used in the inventive compositions have n=20-450, m=0-5, x=1-10 and k=1-10 whereas the traditional polyurethane (meth)acrylates used in the art would have n=0-8, m=1-50, and x=1-10 and no urea group. It is this high number of (R-D) repeating units that imparts the high glass transition temperature (Tg) to the derived coating and in turn the properties the coating has when dried of solvent but not cured. The use of so much polymeric diol in the tradition polyurethane (meth)acrylates simply will not result in a high enough Tg to work in the discovered composition. In addition, discovered polyurethane (meth)acrylate is chain extended with water or a diamine to reach the target molecular weight. This chain extension which forms urea linkages provides impact resistance in the final coating.

According to the invention, the polyurethane film-forming polymers have the formula $C\text{-}(D\text{-}[\text{-}(R\text{-}D)_n\text{-}(P\text{-}D)_m\text{-}]_x E)_k\text{-}C$ wherein:
 i) D is a diisocyanate group,
 ii) R is one or more diol or triol groups having a molecular weight less than or equal to 500 Daltons;
 iii) P is one or more oligomeric diol groups having a molecular weight of from about 500 Daltons to about 3000 Daltons;
 iv) E is a urea group having a molecular weight less than or equal to 500 Daltons;
 v) C is a monohydroxyl functional acrylate group or methacrylate group;
 wherein the equivalent ratio of equivalent ratio of (i) to (ii) is less than 1.5:1; and the equivalent ratio of (i) to (iii) is greater than 15:1; n=20 to 450, m=0 to 5, x=1 to 10, and k=1 to 10;

Non-exclusive examples of diisocyanates useful for forming the diisocyanate group residue D comprise one or more of hexamethylene diisocyanate, trimethyl hexamethylene diisocyanate, bis(4-isocyanatocyclohexyl)methane, isophorone diisoycanate, tetramethylxylene diisocyanate, trimethylhexamethylene diisocyanate, toluene diisocyanate, and isophorone diisoycanate.

Non-exclusive examples of suitable diols and triols useful for forming the diol or triol group residue R comprise one or more of 1,4-butanediol, neopentylglycol, diethylene glycol, 2-methyl-1,3-propanediol, glycerol and trimethylolpropane. Useful diol or triol residues have a molecular weight less than 500 g/mole, preferably less than 250 g/mole, more preferably less than 100 g/mole.

Non-exclusive examples of suitable oligomeric diols useful for forming the oligomeric diol groups P include polyester glycol, polypropylene glycol, polytetramethylene glycol, polycaprolactone glycol, polycarbonate glycol, more preferably polycaprolactone glycol and polycarbonate glycol. The oligomeric diol groups P have a molecular weight of from about 500 to about 3000 Daltons, preferably from about 1000 to about 2000 Daltons.

Non-exclusive examples of suitable components useful for forming the chain extender urea group E include water and ethylenediamine. Preferably the chain extender urea group E has a weight concentration which is less than 0.8% preferably less than 0.6%, more preferably less than 0.4% based on the weight of the polyurethane film-forming polymer. Preferably the urea group comprises an ethylenediamine group.

Non-exclusive examples of suitable mono functional capping alcohol useful for forming the monohydroxyl functional acrylate group or methacrylate residue group have a (meth) acrylate functionality of 4 or less, preferably less than 3, more preferably less than 2, and include 2-hydroxyethyl acrylate, 2-hydroxyethyl methacrylate, hydroxypropyl acrylate, hydroxypropyl methacrylate, 4-hydroxybutyl acrylate, 4-hydroxybutyl methacrylate. N-(2-Hydroxypropyl)methacrylamide and pentaerythritol triacrylate.

A general procedure for forming the polyurethane film-forming polymers is: the non-alcohol solvent(s) and diisocyanate are added into a reactor along with one or more optional antioxidants and one or more optional catalysts. Agitator speed of the reactor is set to 100 rpm. The oligomeric diol and low molecular weight diol or triol are charged into the reactor. Jacket temperature is set to 90° C. The product's molecular weight is monitored with gel permeation chromatography. When the product molecular weight is above 10,000 Daltons, a low molecular weight chain extender is added to form urea form urea groups and increase molecular weight. After reaching the desired molecular weight the product is end-capped with a monohydroxyl functional (meth)acrylate. After all isocyanate groups are consumed, the product is cooled down to 60° C. Once product temperature reaches 60° C. the alcohol solubilizer is added. The solution is allowed to mix for two hours after which the product is drained from the reactor into the appropriate containers for storage.

Non-limiting examples of suitable antioxidants include 2,6-bis(1,1-dimethylethyl)-4-methylphenol, 4-methoxyphenol, pentaerythritol tetrakis(3-(3,5-di-tert-butyl-4-hydroxyphenyl)propionate), pentylenetetrazole, 4-hHydroxy-2,2,6, 6-tetramethylpiperidine, and 1-oxyl and tris(2,4-di-tert-butylphenyl)phosphite.

Non-limiting examples of suitable catalysts include organometallic catalysts such as dibutyltin dilaurade, stannous octoate, dibutyltin diacetate, bismuth neodecanoate and zinc neodecanoate, and tertiary amine catalysts such as; 1,3,5-tris (3-[dimethylamino]propyl)-hexahydro-s-triazine, 1,4-diazabicyclo[2.2.2]octane and N,N-dimethylcyclohexylamine.

In general, the resultant polyurethane polymers have a molecular weight of about 100,000 Daltons or less, preferably 75,000 Daltons or less, and more preferably from about 10,000 to about 50,000 Daltons. In general, the resultant polyurethane polymers have a Tg greater than 0° C., preferably greater than 15° C., more preferably greater than 30° C. Especially useful polyurethane polymers have a Tg of from about 50° C. 10° C. about 100° C., preferably of from about 60° C. about 80° C. In general, the resultant polyurethane polymers have a melting point greater than about 50° C., preferably greater than about 80° C., more preferably greater than about 100° C. The amount of polyurethane film-forming polymer in the liquid, curable coating composition preferably ranges from about 15% to about 50%, more preferably from about 25% to about 40% based on the weight of the coating composition.

An alcohol solubilizer is used to make the polyurethane polymer miscible in a solvent. In general, the alcohol solubilizer is an alcohol with molecular weight less than about 500 g/mole, preferably less than about 300 g/mole, more preferably less than about 150 g/mole. Non-exclusive examples of suitable alcohol solubilizers, include ethanol, 2-propanol and 2-ethylhexanol. The amount of alcohol solubilizer in the liquid, curable coating composition preferably ranges from about 5% to about 25%, more preferably from about 10% to about 15% based on the solids weight of the coating composition. The inclusion of the solubilizer was found to ensure complete dissolution of the high molecular weight polyurethane (meth)acrylate into a wide range of solvents and concentrations to allow a greater degree of freedom in formulation. It has been discovered that this alcohol solubilizer then evaporates with the non-alcohol solvent giving the derived coating the unique property of being chemically resistant to some solvents but still soluble in others. This property allows the end user to easily remove the coating with certain solvent if necessary.

The liquid, curable coating composition then contains a non-alcohol solvent. Preferably the non-alcohol solvent is organic and has a flash point lower than about 80° C., preferably less than about 50° C., more preferably less than about 30° C. Non-exclusive examples of suitable non-alcohol solvents include butan-2-one, heptan-2-one, butyl acetate, ethyl acetate, propyl acetate, acetone, methanol, ethanol, 2-propanol, more preferably butyl acetate and ethyl acetate. Preferably the percentage of solvent is greater than about 20%, more preferably greater than about 40%, and most preferably greater than about 60% by weight based on the weight of the coating composition.

The coating composition according to the invention then contains a visible light absorbing photoinitiator in an amount sufficient to polymerize the polyurethane film-forming polymers when exposed to light energy having a wavelength of about 395 nm or above at an energy level of about 1 $J/cm^2$ or more within this wavelength range. A preferred energy level is from about 5 $J/cm^2$ to about 300 $J/cm^2$, more preferably from about 20 $J/cm^2$ to about 200 $J/cm^2$. Preferred wavelength range is from about 395 nm to about 500 nm. Non-exclusive examples of suitable photoinitiators include one or more phosphene oxides, such as one or more of methanone, 1,1'-(phenylphosphinylidene)bis[1-(2,4,6-trimethylphenyl)-, methanone, (diphenylphosphinyl)(2,4,6-trimethylphenyl)-, phosphinic acid, P-phenyl-P-(2,4,6-trimethylbenzoyl)-, ethyl ester, and bicyclo[2.2.1]heptane-2,3-dione, 1,7,7-trimethyl-, and camphorquinone. These are available commercially under the trade names Irgacure 819, Lucirin TPO, and Lucirin TPO-L. The amount of photoinitiator present is from about 0.1% to about 10%, preferably from about 0.1% to 5% and more preferably from about 0.1% to 2% by weight based on the weight of the coating composition.

The coating composition may optionally additionally comprise one or more components selected from the group consisting of film forming polymers, defoamers, reactive diluents, pigments and adhesion promoters, whose composition and amounts may easily be determinable by those skilled in the art.

The liquid, curable coating composition may be formed by admixing the component parts such as by means of mechanical agitation.

In use, the liquid, curable coating composition is applied onto a suitable substrate, dried to a substantially tack-free coating by evaporation of the non-alcohol solvent and alcohol solubilizer until achieving pencil hardness of about 2 B or less as measured according to ASTM D3363 without any exposure to visible light. The coating derived from a liquid composition is dry to the touch after application to a substrate and evaporation of the solvent within two hours or more preferable less than one hour without exposure to visible light. Typically it has a Mandrel flexibility of about 1.0 inch or less, more preferably about 0.5 inch or less in accordance with ASTM D552 without exposure to visible light. Typically it exhibits an impact resistance of greater than about 48 inch-pounds, more preferably greater than about 72 inch-pounds in accordance with ASTM D552 without exposure to visible light. Typically it exhibits resistance to 2-propanol of greater than about 50 double rubs, preferably greater than about 100 double rubs, more preferably greater than about 150 double rubs in accordance to ASTM method D5402 without exposure to visible light.

The substantially tack-free coating resulting from step II) is then exposed to light energy having a wavelength of 395 nm or above at an energy level of about 1 $J/cm^2$ or more, preferably by exposure to sunlight until the dried and exposed coating has a pencil hardness of about 2H or more as measured according to ASTM D3363. This can usually be accomplished by sunlight exposure for from about 30 minutes to 120 minutes. The substantially tack-free coating exhibits hardening when exposed to visible light for a period of time to a pencil hardness of greater than 3H, preferably a hardness greater than 4H, more preferably greater than 5H, in accordance with ASTM D3363. The visible light exposed coating exhibits less than about 100 double rubs resistance, preferably less than about 50 double rubs, more preferably less than about 25 double rubs resistance to acetone and methylethyl ketone in accordance to ASTM method D5402.

The following non-limiting examples serve to illustrate the invention.

EXAMPLES

The five different coating compositions shown below are prepared in order to compare the properties of the coating derived from the inventive compositions. The high molecular weight polyurethane acrylate used in the composition had an average molecular weight of 41,000 Daltons and whose structure can be described as being according to Formula 2 above with n=45-150, m=1-3, x=1-3 and k=1-10. The Tg of the high molecular weight polyurethane acrylate was measured to be 55-65° C. as measured by dynamic mechanical analysis (DMA).

Comparative Formulas A and B include other ingredients traditionally used in the art. In the case of Formula A this is a low molecular weight trifunctional polyurethane (meth)acrylate typically used to improve hardness and abrasion resistance. Formula B includes a commercially available monofunctional methacrylate monomer with molecular weight of 170 g/mole typically used to increase flexibility and improve adhesion. Comparative Formulas C and D replace the high molecular weight polyurethane acrylate found in the invention formula with other, traditional polyurethane (meth)acrylates. Polyurethane (meth)acrylate 1 is a commercially available aliphatic polyurethane (meth)acrylate with average molecular weight of 14,000 Daltons and whose structure can be described as being according to Formula 1 above with n=0, m=5-7, x=1. Polyurethane (meth)acrylate 2 is another commercially available aliphatic polyurethane (meth)acrylate with average molecular weight of 14,000 and whose structure can be described as being according to Formula 1 above with n=0-5, m=1-5 and x=1-2. Both polyurethane (meth)acrylates have a Tg<0° C. The high molecular weight polyurethane (meth)acrylates used in the new composition can further be differentiated from the two alternate, traditional polyurethane (meth)acrylates by looking at the equivalent ratios and weight percentages of the four main components found in the general structure of Formula 1. As seen in the table below the high molecular weight polyurethane (meth)acrylates are comprised mostly of D and R, where the alternate polyurethane (meth)acrylates are primarily P.

In the following examples, mixed formulas were applied to 0.6 mm thick aluminum substrates using a BYK 10 mil draw down bar. Samples were allowed to dry to a hard, tack-free coating in a dark area to avoid premature exposure to light. Coated substrates underwent physical property testing before and after exposure to different intensities of light. The approximate dry film thickness of the coating for the physical testing was 0.002 inch. Tack-free time is defined by ASTM D1640 7.5.2. Coating was touched every minute until there were no pronounced marks left on the coating after touching. Flexibility is defined by ASTM D552 13.1.2 resistance to cracking. An aluminum substrate coated with the formulation and cured under different conditions. The panel was then slowly bent over a pentagonal Mandrel bend test apparatus. Coating was inspected for cracking and was issued a pass if no cracking was observed after bending. Impact resistance is defined by ASTM D2794. An aluminum substrate was coated with the formulations and cured under different conditions. The coated panel was then placed flat on a universal impact tester. A two pound load was raised incrementally and dropped on the panel. The number reported is the maximum force applied before cracking in the coating was observed. Gloss is test method is defined by ASTM D 523. Gloss of the coatings was measured with a BYK micro-TRI-gloss model number 4430. Pencil hardness is defined by ASTM D3363. Pencil harnesses recorded is the hardest pencil that does not leave a mark on the coating. Abrasion resistance is defined by ASTM D4060. Cast molds of the coating are then placed on a Taber abrasion apparatus and run for 600 cycles with a H-18 abrasion wheel and 250 g weight. Recorded values are the amount of material abraded after 600 cycles.

|   |                    | High Mw Polyurethane (meth)acrylate | Comparative Polyurethane (meth)acrylate 1 | Comparative Polyurethane (meth)acrylate 2 |
|---|--------------------|-------|-------|-------|
| D | Equivalent number  | 38    | 2     | 3     |
|   | wt %               | 61.8% | 16.3  | 18.1  |
| R | Equivalent number  | 30    | 0     | 1     |
|   | wt %               | 27.5% | 0     | 3.1   |
| P | Equivalent number  | 1     | 1     | 1     |
|   | wt %               | 4.8   | 73.2  | 69.1  |
| E | Equivalent number  | 4     | 0     | 0     |
|   | wt %               | 0.3   | 0     | 0     |
| C | Equivalent number  | 3     | 1     | 1     |
|   | wt %               | 5.6%  | 10.5  | 9.7%  |

Invention Formula

|                                                                 | Weight in grams |
|-----------------------------------------------------------------|-----------------|
| High molecular weight Polyurethane (meth)acrylate (synthesized in 50% butyl acetate) | 49 |
| Irgacure 819 photoinitiator                                     | 2.0             |
| Ethyl Acetate                                                   | 49.0            |
| Solubilizer                                                     | 2.5             |

Comparative Formula A

|                                                                 | Weight in grams |
|-----------------------------------------------------------------|-----------------|
| High molecular weight (meth) acrylate (synthesized in 50% butyl acetate) | 24.5 |
| Trifunctional Urethane Acrylate of Mw ~1500                     | 24.5            |
| Irgacure 819 photoinitiator                                     | 2.0             |
| Ethyl Acetate                                                   | 49.0            |
| Solubilizer                                                     | 1.2             |

Comparative Formula B

|                                                                 | Weight in grams |
|-----------------------------------------------------------------|-----------------|
| High molecular weight (meth) acrylate (synthesized in 50% butyl acetate) | 39.5 |
| Tetrahydrofurfuryl Methacrylate (THFMA)                         | 5.0             |
| Irgacure 819 photoinitiator                                     | 2.0             |
| Butyl Acetate                                                   | 4.75            |
| Ethyl Acetate                                                   | 48.75           |
| Solubilizer                                                     | 1.2             |

Comparative Formula C

|                                   | Weight in grams |
|-----------------------------------|-----------------|
| Polyurethane (meth)acrylate 1     | 25.0            |
| Irgacure 819 photoinitiator       | 0.5             |
| Butyl Acetate                     | 25.0            |

Comparative Formula D

|                                   | Weight in grams |
|-----------------------------------|-----------------|
| Polyurethane (meth)acrylate 2     | 25.0            |
| Irgacure 819 photoinitiator       | 0.5             |
| Butyl Acetate                     | 25.0            |

Results Tables:

TABLE 1

Without any light curing

|                             | Formula |   |   |   |   |
|-----------------------------|---------|---|---|---|---|
|                             | Invention Formula | Comparative Formula A | Comparative Formula B | Comparative Formula C | Comparative Formula D |
| Pencil hardness             | 10 B    | 2 B | 3 B | none | none |
| Flexibility (Mandrel bend)  | Pass 3/8" | Pass 3/8" | Pass 3/8" | none | none |
| Impact resistance           | 98 inch-pounds | 1.5 inch-pounds | 1.5 inch-pounds | none | none |
| Gloss (20° and 60°)         | 102, 132 | 70, 129 | 54.2, 121 | none | none |
| Tack free                   | 12 minutes | 19 minutes | 35 minutes | Remained Liquid | Remained Liquid |

TABLE 2

Curing conditions—Ambient Sunlight (Total Energy 30 J/cm²)

| | formula | | | | |
|---|---|---|---|---|---|
| | Invention Formula | Comparative Formula A | Comparative Formula B | Comparative Formula C | Comparative Formula D |
| pencil hardness | 6 H | 5 H | 5 H | cured tacky | cured tacky |
| Flexibility (Mandrel bend) | Fail 1" | Fail 1" | Pass 3/8" | cured tacky | cured tacky |
| Impact resistance | 1.5 inch-pounds | 1.5-inch pounds | 1.5 inch-pounds | cured tacky | cured tacky |
| Gloss (20° and 60°) | 65.7, 96.0 | 83.1, 111.0 | 33.9, 90.0 | cured tacky | cured tacky |
| Abrasion resistance, average mass of coating lost after 600 cycles | 0.037 g | Total coating failure after 300 cycles | 0.032 g | cured tacky | cured tacky |

TABLE 3

Curing conditions—EC-5000 H-Bulb (Total Energy 9 J/cm²)

| | formula | | | | |
|---|---|---|---|---|---|
| | Invention Formula | B | C | D | E |
| pencil hardness | 2 H | H | 4 H | Not Tested | Not Tested |

SUMMARY

The coating derived from the invention formula shows a very fast dry time to a tack-free surface with good flexibility and gloss. After exposure to sunlight the pencil hardness of the coating increases dramatically, even higher than the coating hardness when cured with traditional UV curing equipment of higher energy. The coating also shows very good abrasion resistance. While some of the coatings derived from the comparative examples have these properties as well, none have them all. Comparative Formula A had extremely poor abrasion resistance after sunlight curing and Comparative Formula B had almost triple the tack free time. Comparative Formula C and D, made with two alternate, traditional polyurethane (meth)acrylates does not result in a tack free surface even after sunlight curing.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A liquid, curable coating composition comprising in admixture:
   (a) one or more polyurethane film-forming polymers having the formula

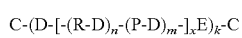

wherein:
   i) D is a residue of a diisocyanate group,
   ii) R is a residue of one or more diol or triol groups having a molecular weight less than or equal to 500 Daltons;
   iii) P is a residue of one or more oligomeric diol groups having a molecular weight of from about 500 Daltons to about 3000 Daltons;
   iv) E is a residue of a urea group having a molecular weight less than or equal to 500 Daltons;
   v) C is a residue of a monohydroxyl functional acrylate group or methacrylate group;
   wherein the equivalent ratio of (i) to (ii) is less than 1.5:1; and the equivalent ratio of (i) to (iii) is greater than 15:1;
   n=20 to 450, m=01 to 5,
   x=1 to 10, and k=1 to 10;
   b) an alcohol solubilizer;
   c) a non-alcohol solvent;
   (d) a photoinitiator in an amount sufficient to polymerize the polyurethane film-forming polymers when exposed to light energy having a wavelength of 395 nm or above at an energy level of about 1 J/cm² or more.

2. The coating composition according to claim 1, wherein the amount of polyurethane film-forming polymer is from about 15% to about 50% based on the weight of the coating composition.

3. The coating composition according to claim 1, wherein the residue of the diisocyanate group comprises a residue of one or more of hexamethylene diisocyanate, trimethyl hexamethylene diisocyanate, bis(4-isocyanatocyclohexyl)methane, isophorone diisoycanate, tetramethylxylene diisocyanate, trimethylhexamethylene diisocyanate, toluene diisocyanate, and isophorone diisoycanate.

4. The coating composition according to claim 1, wherein the residue of the diol or triol group has a molecular weight of about 500 g/mole or less.

5. The coating composition according to claim 1, wherein the residue of the oligomeric diol has a molecular weight of from about 1000 Daltons to about 2000 Daltons.

6. The coating composition according to claim 1, wherein the residue of the urea group is formed by reaction of ethylenediamine or water with the diisocyanate group (D).

7. The coating composition according to claim 1, wherein the residue of the urea group is present in an amount of less than about 0.8% based on the weight of the polyurethane film-forming polymer.

8. The coating composition according to claim 1, wherein the residue of the acrylate group or methacrylate group comprises a residue of one or more of 2-hydroxyethyl acrylate, 2-hydroxyethyl methacrylate, hydroxypropyl acrylate, hydroxypropyl methacrylate, 4-hydroxybutyl acrylate, 4-hydroxybutyl methacrylate, N-(2-Hydroxypropyl)methacrylamide and pentaerythritol triacrylate.

9. The coating composition according to claim 1, wherein the polyurethane polymers have a molecular weight of about 100,000 Daltons or less.

10. The coating composition according to claim 1, wherein the polyurethane polymers have a Tg of about 0° C. or greater.

11. The coating composition according to claim 1, wherein the polyurethane polymers have a melting point of about 50° C. or greater.

12. The coating composition according to claim 1, wherein the non-alcohol solvent is organic and has a flash point lower than about 80° C.

13. The coating composition according to claim 1, wherein the non-alcohol solvent is present in an amount of about 20% or more based on the weight of the coating composition.

14. The coating composition according to claim 1, wherein the alcohol solubilizer as a molecular weight of about 500 g/mole or less.

15. The coating composition according to claim 1, wherein the photoinitiator comprises one or more of methanone, 1,1'-(phenylphosphinylidene)bis[1-(2,4,6-trimethylphenyl)-, methanone, (diphenylphosphinyl)(2,4,6-trimethylphenyl)-, phosphinic acid, P-phenyl-P-(2,4,6-trimethylbenzoyl)-, ethyl ester, and bicyclo[2.2.1]heptane-2,3-dione, 1,7,7-trimethyl-, and camphorquinone.

16. The coating composition according to claim 1, wherein the photoinitiator is present in an amount of from about 0.1% to about 10% by weight based on the weight of the coating composition.

17. The coating composition according to claim 1, additionally comprising one or more components selected from the group consisting of film forming polymers, defoamers, pigments and adhesion promoters.

18. A method of forming a substantially tack-free coating which comprises:
   I) forming a liquid, curable coating composition comprising in admixture:
   (a) one or more polyurethane film-forming polymers having the formula $C\text{-}(D\text{-}[\text{-}(R\text{-}D)_n\text{-}(P\text{-}D)_m\text{-}]_x E)_k\text{-}C$ wherein:
   i) D is a residue of a diisocyanate group,
   ii) R is a residue of one or more diol or triol groups having a molecular weight less than or equal to 500 Daltons;
   iii) P is a residue of one or more oligomeric diol groups having a molecular weight of from about 500 Daltons to about 3000 Daltons;
   iv) E is a residue of a urea group having a molecular weight less than or equal to 500 Daltons;
   v) C is a residue of a monohydroxyl functional acrylate group or methacrylate group;
   wherein the equivalent ratio of (i) to (ii) is less than 1.5:1; and the equivalent ratio of (i) to (iii) is greater than 15:1; n=20 to 450, m=01 to 5, x=1 to 10, and k=1 to 10;
   b) an alcohol solubilizer;
   c) a non-alcohol solvent;
   (d) a photoinitiator in an amount sufficient to polymerize the polyurethane film-forming polymers when exposed to light energy having a wavelength of 395 nm or above at an energy level of about 1 J/cm² or more;
   II) applying the coating composition onto a substrate following by evaporating the non-alcohol solvent and alcohol solubilizer to form substantially tack-free coating;
   III) exposing the composition resulting from step II) to light energy having a wavelength of 395 nm or above at an energy level of about 1 J/cm² or more.

19. The method according to claim 18, wherein the substantially tack-free coating formed after evaporation of non-alcohol solvent and alcohol solubilizer has a pencil hardness of about 2B or less as measured according to ASTM D3363.

20. The method according to claim 18, wherein the coating resulting from step III) has a pencil hardness of about 2H or more as measured according to ASTM D3363.

* * * * *